United States Patent
Menashe

(10) Patent No.: US 10,136,900 B2
(45) Date of Patent: Nov. 27, 2018

(54) PNEUMATIC TOURNIQUET

(71) Applicant: M.A.S. MED GLOBAL LTD, Rishon Lezion (IL)

(72) Inventor: Shaked Menashe, Cfar Varburg (IL)

(73) Assignee: M.A.S. MED GLOBAL LTD, Rishon Lezion (IL)

( * ) Notice: Subject to any disclaimer, the term of this patent is extended or adjusted under 35 U.S.C. 154(b) by 81 days.

(21) Appl. No.: 14/894,047

(22) PCT Filed: May 23, 2014

(86) PCT No.: PCT/IL2014/050465
§ 371 (c)(1),
(2) Date: Nov. 25, 2015

(87) PCT Pub. No.: WO2014/191987
PCT Pub. Date: Dec. 4, 2014

(65) Prior Publication Data
US 2016/0106439 A1    Apr. 21, 2016

Related U.S. Application Data

(60) Provisional application No. 61/827,601, filed on May 26, 2013.

(30) Foreign Application Priority Data

Apr. 7, 2014 (IL) .......................................... 231979

(51) Int. Cl.
| | |
|---|---|
| *A61B 17/135* | (2006.01) |
| *G01S 19/17* | (2010.01) |
| *A61B 17/132* | (2006.01) |
| *A61B 17/00* | (2006.01) |
| *A61B 90/00* | (2016.01) |

(52) U.S. Cl.
CPC ........ *A61B 17/135* (2013.01); *A61B 17/1355* (2013.01); *G01S 19/17* (2013.01); *A61B 17/1327* (2013.01); *A61B 2017/00115* (2013.01); *A61B 2017/00734* (2013.01); *A61B 2090/061* (2016.02); *A61B 2090/0807* (2016.02)

(58) Field of Classification Search
CPC .. A61B 17/135; A61B 17/1355; A61B 17/132
See application file for complete search history.

(56) References Cited

U.S. PATENT DOCUMENTS

| | | | |
|---|---|---|---|
| 1,447,967 A * | 3/1923 | Rutledge ................. | A44B 11/25 24/163 R |
| 2,839,062 A * | 6/1958 | Jordan .................... | A61B 17/135 606/202 |
| 2,841,149 A | 7/1958 | Marsden | |
| 5,356,412 A | 10/1994 | Golds et al. | |
| 7,892,253 B2 | 2/2011 | Esposito et al. | |
| 2003/0139696 A1 | 7/2003 | Boukanov et al. | |
| 2007/0191881 A1* | 8/2007 | Amisar ............... | A61B 17/1355 606/203 |
| 2008/0281351 A1 | 11/2008 | Croushorn et al. | |
| 2012/0265240 A1* | 10/2012 | Ganske ............... | A61B 17/1325 606/202 |
| 2013/0245673 A1 | 9/2013 | McEwen et al. | |
| 2014/0336697 A1* | 11/2014 | Masaki ................ | A61B 17/135 606/203 |
| 2015/0201948 A1* | 7/2015 | Kornowski ........ | A61B 5/02042 606/203 |
| 2016/0022269 A1* | 1/2016 | Ganske ................ | A61B 17/135 606/202 |

FOREIGN PATENT DOCUMENTS

| | | |
|---|---|---|
| CN | 2875336 Y | 3/2007 |
| CN | 201175359 Y | 1/2009 |
| CN | 201469343 U | 5/2010 |
| CN | 201782793 U | 4/2011 |
| GB | 713132 | 8/1954 |
| TW | 201311204 A | 3/2013 |
| WO | WO 91/18571 A1 | 12/1991 |
| WO | WO 2005/0091718 A2 | 10/2005 |
| WO | WO 2011/001431 A1 | 1/2011 |
| WO | WO 2014/023960 A1 | 2/2014 |

OTHER PUBLICATIONS

PCT International Search Report, PCT Application No. PCT/IL2014/050465, dated Sep. 3, 2014, 4 pages.
PCT Written Opinion, PCT Application No. PCT/IL2014/050465, dated Sep. 3, 2014, 6 pages.
European Extended Search Report, European Application No. 14803638.7, dated Feb. 10, 2017, 9 pages.

* cited by examiner

*Primary Examiner* — Julie A Szpira
(74) *Attorney, Agent, or Firm* — Fenwick & West LLP

(57) ABSTRACT

A compressed gas container and a flow control unit are retained within a rigid housing of a control device locally attached to an inflatable strap of a pneumatic tourniquet. The flow control unit, when triggered, is configured to selectively supply a dose of pressurized gas discharged from the gas container to an internal strap cavity, to achieve a predetermined cavity pressure for applying a required hemorrhage suppressing force onto a limb. In one embodiment, a strap restraining unit permits displacement of a free end of the strap without resistance until assuming a predetermined length sufficient to apply the hemorrhage suppressing force and which corresponds to a disposition of a restraining element at which it is in sufficiently close pressing relation with the strap to cause it to become restrained. The tourniquet is deployable in one embodiment by engaging an unattached end of a buckle frame with a large-area protruding part.

22 Claims, 16 Drawing Sheets

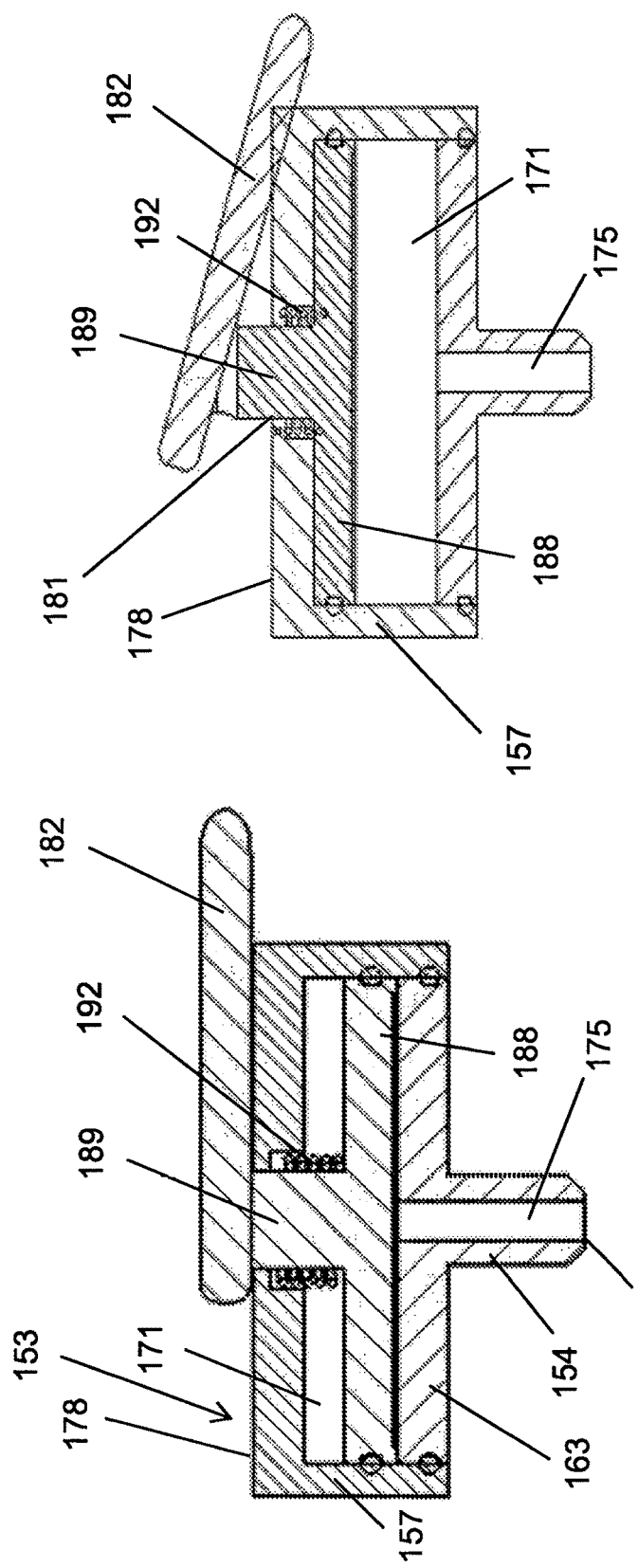

PNEUMATIC TOURNIQUET

RELATED APPLICATIONS

This application is a 35 U.S.C. 371 national stage filing of International Application No. PCT/IL2014/050465, filed on May 23, 2014, which claims priority to Israeli Patent Application No. 231979 filed on Apr. 7, 2014, and U.S. Provisional Patent Application No. 61/827,601, filed on May 26, 2013. The contents of each application are hereby incorporated by reference.

FIELD OF THE INVENTION

The present invention relates to the field of inflatable tourniquets. More particularly, the invention relates to a tourniquet that is inflatable by means of a control device attached to a strap for applying a hemorrhage suppressing force.

BACKGROUND OF THE INVENTION

A tourniquet is a well known device for suppressing hemorrhaging. A bandage twisted tight by an implement such as a stick is traditionally used to apply pressure onto an artery and to therefore stop the flow of blood through a limb.

During emergency situations, when a wounded person experiencing a severe loss of blood is alone, the blood flow can be occluded only if the hemorrhage suppressing force can be self applied. A wound victim, however, is generally physically limited and is not always able to apply the required hemorrhage suppressing force. The actual force needed to suppress hemorrhaging is of course dependent upon the thickness of the limb and upon the depth of the artery within the limb. If the applied force is excessive, bones, for example the fibula and tibia bones located within the leg, are liable to be fractured, and damage to soft tissue, such as late soft tissue complications, is liable to result.

An important consideration for a medic or any other person applying the hemorrhage suppressing force is proper documentation as to the time when the hemorrhage suppressing force was initiated. Ischemia develops in the limb as a result of prolonged arterial occlusion. Physiological and anatomical studies have shown that irreversible muscle damage starts after 3 hours of ischemia and is nearly complete at 6 hours, following occlusion of the artery. As a wound victim suffers the risk of amputation when ischemia develops, it is imperative to indicate the time when the hemorrhage suppressing force was initiated, so that the wound victim can be quickly dispatched to a hospital for treatment and for release of the hemorrhage suppressing force. A wound victim usually does not have the presence of mind to write on the strap the time when the self-applied hemorrhage suppressing force was initiated, and furthermore is generally incapable of applying the required constant hemorrhage suppressing force.

U.S. Pat. No. 7,892,253 discloses a tourniquet for emergency use, and may be applied by using only one hand. The tourniquet comprises an outer sleeve, a buckle connected to one end of the outer sleeve, an inner strap in slidable engagement with the outer sleeve, and a windlass rod connected to the inner strap. The buckle has a raised intermediate bar and a tooth for contacting the outer sleeve. The outer surface of the outer sleeve includes hook and loop structures, in order to detachably interlock first and second portions of the outer surface together while being adjusted to different sized limbs, after the other end of the outer sleeve is passed through the buckle and is secured around the limb. The windlass is rotated to apply a tensile force to the inner strap and a circumferentially applied compression force to the limb for restricting the flow of blood.

Such a tourniquet suffers from several drawbacks. Firstly, the time for feeding the outer sleeve through the buckle and for being secured to the wounded limb is relatively lengthy. Secondly, the tourniquet does not facilitate speedy deployment to trapped limbs. In order to be deployed to trapped limbs, the outer sleeve has to be manually disengaged from the buckle and subsequently passed around the limb and reengaged with the buckle before being tightened. Even a few seconds of delay as a result of this deployment process, in addition to the limited concentration and dexterity of the person attempting to perform a hemorrhage suppressing operation during high stress conditions, particularly the wounded victim during one-handed deployment, can cause fatal blood loss.

Thirdly, there is no control as to the instantaneous hemorrhage suppressing force being applied. The bleeding artery will not be sufficiently occluded if the hemorrhage suppressing force is less than the required magnitude. On the other hand, damage to soft tissue, muscles, nerves and bones within the wounded limb is liable to result, particularly due to the narrow dimension of the strap of approximately 2.5 cm that cuts into the skin, if an excessive force is applied. Due to the pain caused by narrow strap, the wounded victim will tend not to apply a sufficiently high self-applied hemorrhage suppressing force. Thus this prior art tourniquet can be reliably deployed only by an experienced medic or any other medical practitioner.

Moreover, the hook and loop structures needed for adjustment to different sized limbs will not be effectively interlocked in a harsh environment, such as mud and water, and have difficulty to be interlocked during conditions of darkness due to the difficulty in adequately seeing the structures.

Various pneumatic tourniquets are known from the prior art, including GB 713132, US 2013/0245673, TW 201311204 and CN 2875336.

WO 2014/023960 discloses an inflation system for a tourniquet that comprises an unprotected pressurized gas bottle coupled to an inlet port and protruding from the edge of the cuff, a movable piston located between the inlet port and outlet port, and a spring recessed within the chamber that cooperates with the piston to resist backward movement of the piston relative to the inlet port. Disengagement of the piston from the inlet port occurs when the gas pressure in the bottle is greater than a combination of the internal pressure within the bladder and the bias exerted by the spring.

As the gas bottle is unprotected and liable to be damaged, this inflation system is not suitable for use in a battlefield environment. Also, the gas bottle cannot be realistically used for more than one hemorrhage suppression operation since the gas pressure in the bottle is generally significantly greater than the combination of the internal pressure within the bladder and the bias exerted by the spring, and therefore a large majority of the compressed gas will be discharged during the course of a single hemorrhage suppression operation.

It is an object of the present invention to provide a pneumatic tourniquet by which the strap applying a hemorrhage suppressing force is inflatable to a controlled pressure.

It is an additional object of the present invention to provide a pneumatic tourniquet that can be deployed much quicker than prior art devices.

It is an additional object of the present invention to provide a pneumatic tourniquet that can be self-deployed.

It is yet an additional object of the present invention to provide a pneumatic tourniquet that can be reliably deployed in harsh environments such as in mud or water.

It is yet an additional object of the present invention to provide a pneumatic tourniquet having a flow control unit that is completely reusable.

Other objects and advantages of the invention will become apparent as the description proceeds.

SUMMARY OF THE INVENTION

The present invention provides an intelligent pneumatic tourniquet, comprising a control device which is locally attached to an inflatable strap having an internal cavity, for achieving a predetermined pressure within said cavity and for thereby applying a required hemorrhage suppressing force onto a limb with which said strap is engaged.

Said control device comprises a compressed gas container, a flow control unit that is in fluid communication with said container and with said internal cavity, and a rigid housing within which said compressed gas container and said flow control unit are retained, wherein said flow control unit, when triggered, is configured to selectively supply a dose of pressurized gas discharged from said gas container to said internal cavity.

The flow control unit ensures that a substantially constant controlled hemorrhage suppressing force will be applied onto the limb with which the strap is engaged, to prevent additional injury to a wound victim while maintaining satisfactory hemorrhage suppression.

The flow control unit preferably is triggerable by an initiating force applied by a strap restraining unit. The strap restraining unit is configured to permit displacement of a free end of the strap without resistance until said free end assumes a predetermined length which is sufficient to apply the hemorrhage suppressing force and to cause the strap to become restrained by a strap derived force.

In one aspect, the strap restraining unit cooperates with the flow control unit so as to facilitate maximum tensioning of the strap, puncturing of the gas container membrane and regulating the pressure within the internal cavity to maintain the predetermined pressure in response to a single user motion, e.g. a one hand motion.

In one aspect, the strap restraining unit cooperates with the flow control unit so as to facilitate maximum tensioning of the strap, puncturing of the gas container membrane and initiate timing of a hemorrhage suppressing operation in response to a single user motion. The elapsed time of the hemorrhage suppressing operation is visible on a digital timer mounted in the housing of the control device, in order to avoid irreversible ischemia-caused muscle damage to the subject who is undergoing the hemorrhage suppressing operation.

In one aspect, the control device comprises a circuit board for supporting the functionality of one or more electronic devices that are intended to assist a wounded victim.

The tourniquet is able to compactly stored in a sufficiently small package to allow it to be carried in a pocket or in a first aid kit, for use in an ambulance, emergency services, hospitals and military applications. The package can also be attached to a soldier's military gear, a construction worker's harness, or to a person's clothing.

The present invention is also directed to a tourniquet equipped strap restraining unit, comprising a guide element for introduction therethrough of a strap adapted to apply a hemorrhage suppressing force onto a limb of a wounded subject, and a restraining element which is movable in response to a strap derived force resulting from displacement of said strap through said strap restraining unit, wherein said strap restraining unit is configured to permit displacement of a free end of said strap without resistance until said free end assumes a predetermined length which is sufficient to apply the hemorrhage suppressing force and which corresponds to a disposition of said restraining element at which it is in sufficiently close pressing relation with said strap to cause said strap to become restrained.

The strap restraining unit may also comprise an initiating element that is also movable in response to the strap derived force, wherein the strap is a pneumatically inflatable strap and said initiating element is displaceable to a position at which it is capable of applying a force to a trigger for actuating inflation of the strap.

The present invention is also directed to a method for deploying a tourniquet, comprising the steps of providing a tourniquet with a strap, a large-area part locally attached to, and protruding outwardly from, a first end of said strap, and a buckle frame attached to a second end of said strap such that a strap free end portion extends from, and is movably engageable with, said buckle frame; placing said first strap end in abutting relation with a wounded limb to which a hemorrhage suppressing force is desired to be applied; wrapping said strap about said limb until said buckle frame is adjacent to said protruding part; engaging an unattached end of said buckle frame with said protruding part; extending said strap free end portion until said strap becomes sufficiently tensioned so as to apply circumferential pressure onto said limb and to induce hemorrhage suppression.

BRIEF DESCRIPTION OF THE DRAWINGS

In the drawings:

FIG. 23 is a vertical cross sectional view of the piston assembly used in conjunction with the flow control unit of FIG. 20, shown in a normal, non-limiting position;

FIG. 24 is a vertical cross sectional view of the flow control unit of FIG. 20, cut along a plane coinciding with the longitudinal axis of a gas container, which is shown after being puncture and a predetermined pressure has been achieved; and FIG. 25 is a vertical cross sectional view of the piston assembly used in conjunction with the flow control unit of FIG. 20, shown in a limiting position.

DETAILED DESCRIPTION OF PREFERRED EMBODIMENTS

The present invention is an intelligent pneumatic tourniquet for rapidly inflating the strap applying a hemorrhage suppressing force to a constant controlled pressure. A control device is locally attached to the strap, which is configured with an inflatable sleeve. The control device comprises a flow control unit for ensuring that a required dose of pressurized gas, when triggered, will be discharged into the sleeve, and a timer for indicating to a medic the exact time when the hemorrhage suppressing force was initiated, in order to avoid irreversible muscle damage resulting from prolonged ischemia. The discharged dose of pressurized gas is controlled to generate a single predetermined force that is suitable for rapidly and reliably suppressing hemorrhaging in all limbs, without causing bodily damage.

Figure 1:
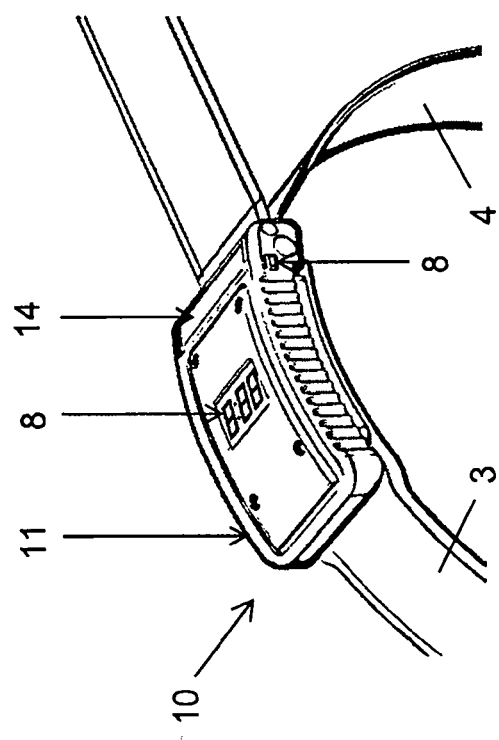
FIG. 1 is a perspective view of a tourniquet according to one embodiment of the present invention.

FIG. 1 illustrates the intelligent tourniquet, generally designated by numeral 10, according to one embodiment of the present invention. Tourniquet 10 comprises an inflatable strap 3, a closed and self contained control device 5 configured as a protruding part, e.g. rectangular, for inflating strap 3 to a controlled pressure, a visible digital timer 8 mounted within the upper surface of control device 5, a removable buckle frame 11 of the same shape as, and engageable with, the periphery of control device 5 for triggering the hemorrhage suppressing force, and a strap release lever 14 integrally formed with buckle frame 11 for selectively releasing the hemorrhage suppressing force.

Strap 3 is made of elongated flexible material, such as a woven fabric that is substantially puncture resistant so as to be suitable for use by soldiers, and is preferably imparted with absorbent material for absorbing exudate from a wounded artery. The strap is generally formed with a cavity into which the pressurized gas for inflating the strap is dischargeable. The strap preferably, but not necessarily, has a relatively wide dimension of at least 4.5 cm, e.g. 5 cm, to ensure that it will not cut into the skin, as opposed to prior art tourniquets having much narrower straps, when the relatively high hemorrhage suppressing force is applied. The wider strap contributes to a reduced but effective pressure being applied to a bodily portion while achieving blood flow control.

Strap 3 may comprise two sleeves such that the inner sleeve that receives the pressurized gas is inserted within the entire length of the outer protective sleeve. Alternatively, the sleeve may be formed of two pieces that are attached together at common lateral ends thereof to define the cavity.

A schematically illustrated pressure relief valve 22 in fluid communication with the internal cavity may be operatively connected to strap 3, adjacent to control device 5. Pressure relief valve 22, which is generally manually actuated, although electrical actuation is also within the scope of the invention, is used at the conclusion of a hemorrhage suppression operation to sufficiently lower the gas pressure within the internal cavity to a level that will allow tourniquet 10 to be removed from the subject and to be deployed on another subject, if necessary. Alternatively, pressure relief valve 22 may be operatively connected to the flow control unit.

The free end 4 of strap 3 is fed within an opening below the front, or user accessible, wall 8 of a strap adjustment chamber 6, which is abuttable with control device 5, passing around pin 9 rotatably mounted in a side wall of strap adjustment chamber 6, as shown in the cross section of FIG. 2. Free end 4 of strap 3 exits strap adjustment chamber 6 above front wall 8, and is contactable by detent 17, e.g. having a thin narrowing terminal end, for preventing additional extension of the free end 4. Detent 17, which is rotatably mounted by pin 18 onto strap release lever 14, is separated from free end 4 when lever 14 is released, in order to adjust the length of free end 4.

Figure 3:
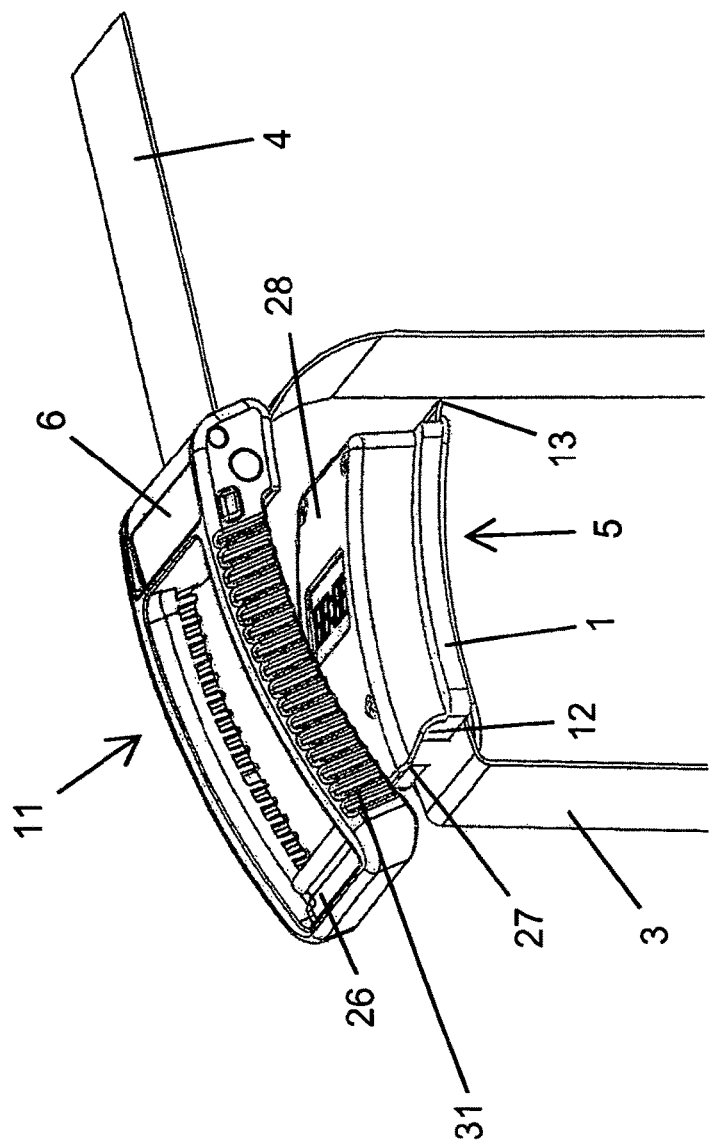
FIG. 3 is a perspective view of the tourniquet of FIG. 1 when the buckle frame is separated from the control device.

Control device 5 and buckle frame 11 are shown in greater detail in FIG. 3. The interiorly positioned, substantially planar base 1 of control device 5 is fixedly attached to one longitudinal end 13 of strap 3, along one face thereof, and the housing of control device 5 protrudes from base 1. While the front wall 2 of control device 5 from which the trigger protrudes is substantially perpendicular to base 1, rear wall 12 thereof is oblique, extending away from front wall 2 to define an engageable portion 27 at the junction with the outer planar surface 28 of the control device for engagement with unattached end 26 of buckle frame 11. The side walls of buckle frame 11 may be configured with a plurality of ribs 31, to facilitate engagement with the rim and side walls of control device 5.

Figure 2:
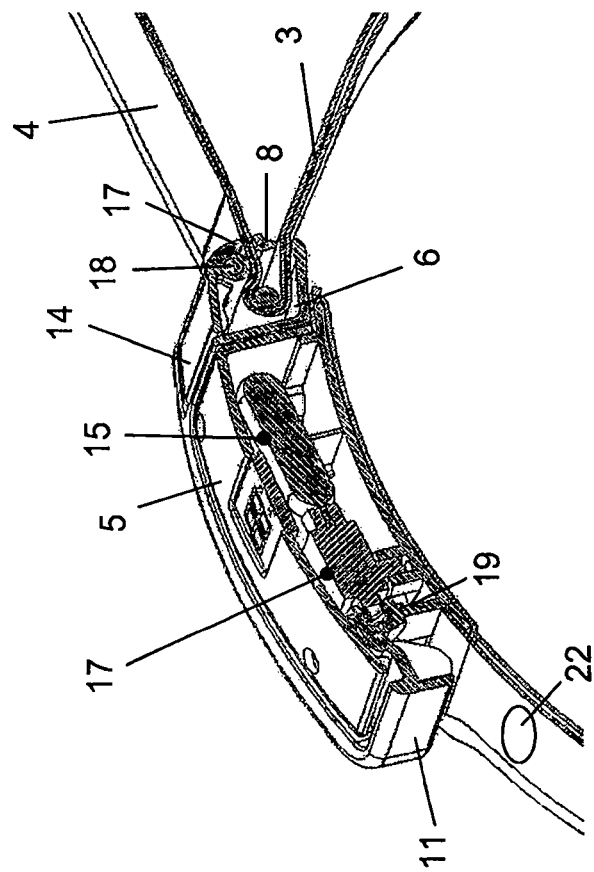
FIG. 2 is a perspective, cross sectional view of the tourniquet of FIG. 1.

The apparatus for controllably generating the hemorrhage suppressing force is housed in control device 5 and is schematically shown in FIG. 2, comprising a replaceable compressed gas container 15, for example containing compressed carbon dioxide, a flow control unit 17 through which the discharged compressed gas passes, and a trigger 19 for controllably actuating gas dispenser 17.

By virtue of its novel configuration, the tourniquet 20 may be rapidly deployed, and even self deployed, as shown in FIGS. 4-8. Tourniquet 20 may be an intelligent pneumatic tourniquet, or alternatively a tourniquet by which the hemorrhage suppressing force is manually applied.

Figure 4:
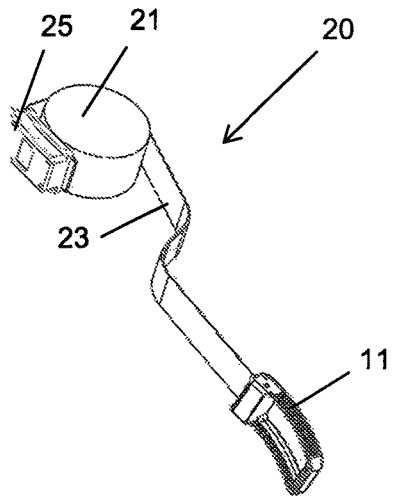
FIGS. 4-8 illustrate five stages, respectively, of deploying the tourniquet of FIG. 1 on the limb of a subject in order to apply the hemorrhage suppressing force.
Figure 5:
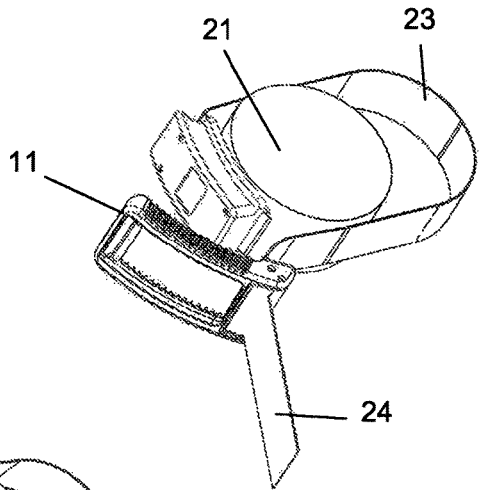
Figure 6:
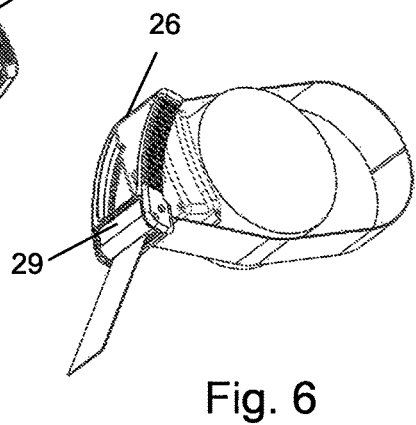
Figure 7:
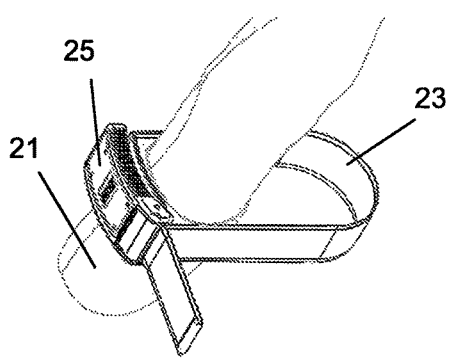
Figure 8:
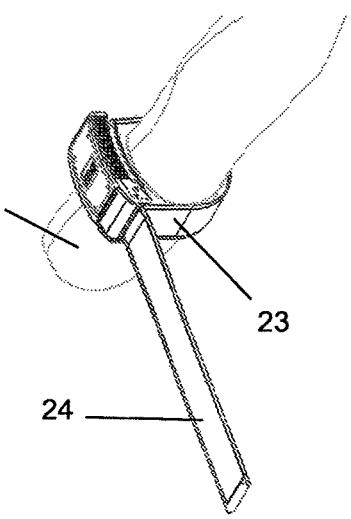

Strap 23 of the undeployed tourniquet is shown in FIG. 4 to extend from the unengaged protruding part 25 to buckle frame 11. After protruding part 25 is placed on a schematically illustrated wounded limb 21 to which a hemorrhage suppressing force is desired to be applied, strap 23 is wrapped about limb 21, as shown in FIG. 5, until buckle frame 11, from which extends a short strap free end portion 24, is adjacent to protruding part 25. The unattached end 26 of buckle frame 11 is then placed in engagement with easily engageable, large-area protruding part 25, as shown in FIG. 6, after which the strap adjustment portion including the strap-connected end 29 thereof is placed in engagement with protruding part 25, as shown in FIG. 7. At this stage, strap 23 loosely encircles limb 21, and is adjustable to fit many different sized subjects. Upon extending the strap free end portion 24 as shown in FIG. 8, strap 23 becomes sufficiently tensioned so as to apply circumferential pressure onto limb 21 and to induce hemorrhage suppression.

The ability of highly visible protruding part 25 to be easily engaged by buckle frame 11 facilitates reliable deployment and adjustment in harsh environments such as in mud or water or during conditions of darkness when protruding part 25 can be easily felt, as opposed to prior art tourniquets that employ hook and loop structures whose interlocking characteristics deteriorate in such harsh environments.

When tourniquet 20 is an intelligent pneumatic tourniquet, the control device becomes automatically triggered after the strap free end portion is sufficiently extended, as will be described hereinafter.

This arrangement facilitates speedy deployment to trapped limbs whose hand or other extremity is covered with rubble or is otherwise inaccessible, whereby the strap is passed around the trapped limb and then the buckle frame is engaged with the readily accessible protruding part.

Figure 9:
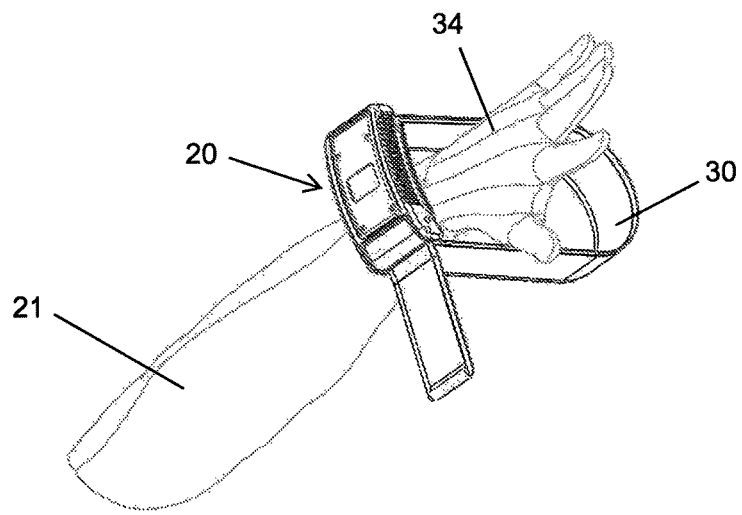
FIG. 9 is a perspective view of the tourniquet of FIG. 1 while the buckle frame is pre-engaged with the control device and introduced over the hand of a subject.

When the buckle frame of tourniquet 20 is pre-engaged with the protruding part to define the looped structure 30 shown in FIG. 9, in anticipation of an injury inflicting event, it may therefore be immediately introduced over hand 34 of a wound victim and then positioned on the wounded limb 21, in order to speedily apply the hemorrhage suppressing force. The strap is subsequently tensioned, similarly as shown in FIGS. 7 and 8.

Figure 10:
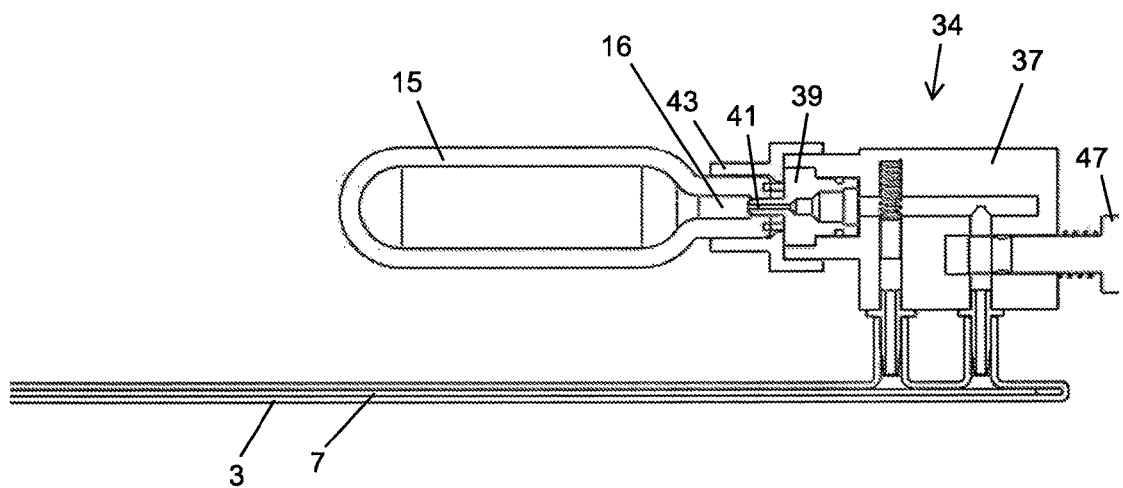
FIG. 10 is a schematic illustration of a flow control unit that interfaces with a compressed gas container and the internal cavity of a pneumatically inflatable strap.
Figure 11:
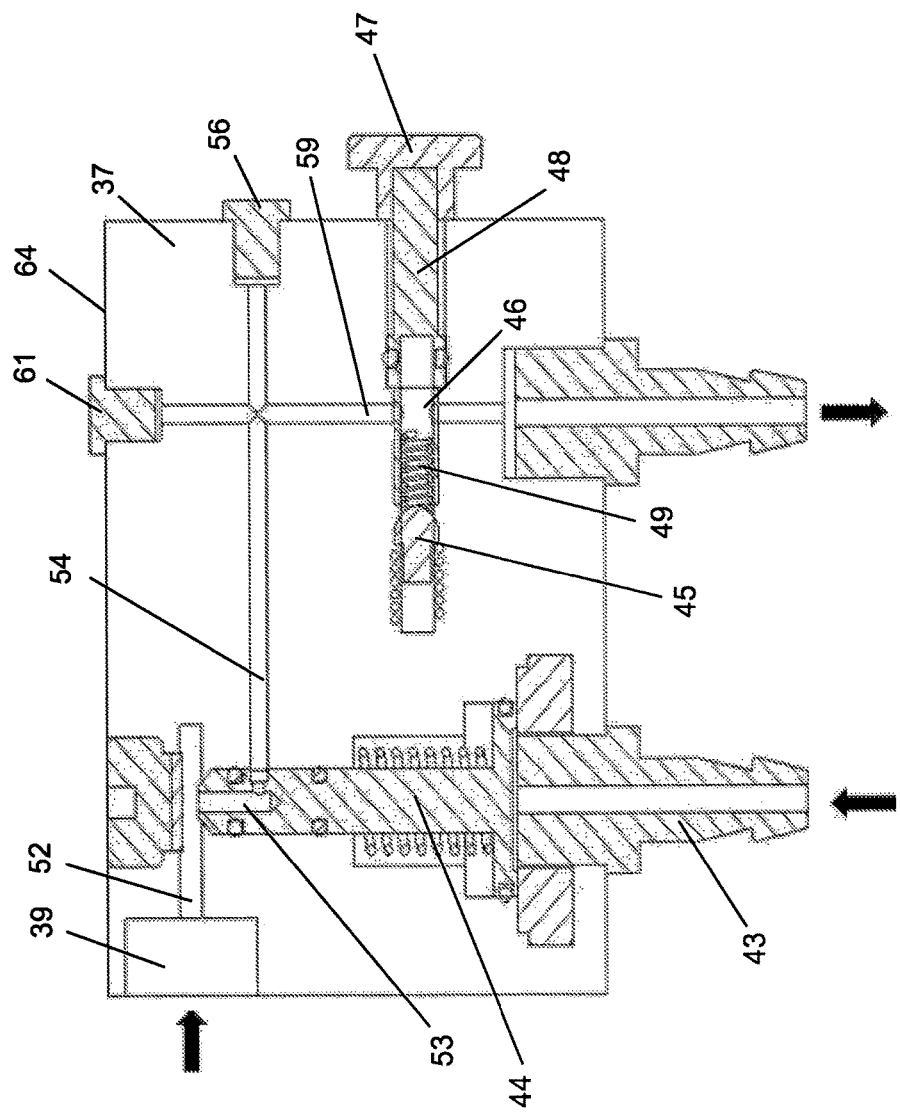
FIG. 11 is a cross sectional view of the flow control unit of FIG. 10.

Reference is now made to FIGS. 10 and 11, which schematically illustrate an exemplary flow control unit 34. Flow control unit 34 comprises a monolithic block structure 37 formed with conduits and recesses in which are mounted flow control elements. In recess 39 is mounted a hollow puncture pin 41, which extends to the interior of threaded cavity 43. When compressed gas container 15 is threadedly engaged to a fullest extent within cavity 43, seal element 16 becomes punctured, to permit the discharged gas to flow through flow control unit 34 into the internal cavity 7 of strap 3.

Fitted in block structure 37 is an inlet fitting 42 for directing the discharged gas to the strap cavity, an outlet fitting 43 in communication with the strap cavity, a control valve 44 receiving gas flowing from outlet fitting 43, and an actuator valve 45 terminating with a flange 47 functioning as the trigger.

A first longitudinal conduit 52 extends from recess 39 in communication with puncture pin 41 to control valve 44, and a second longitudinal conduit 54 extends from control valve 44 to stopper element 56 at the periphery of block structure 37. A vertical conduit 53 interfaces with both first conduit 52 and second conduit 54. Another vertical conduit 59 extending from inlet fitting 42 to stopper 61 at the outer face 64 of block 37 crosses both actuator valve 45 and second conduit 54.

Actuator valve 45 has a slidable stem 48, which is attached to spring connected occluding element 49. When abutment head 47 of actuator valve 45 is in a retracted position, conduit 59 is occluded and compressed gas is prevented from being discharged to the strap's internal cavity. Upon being triggered, abutment head 47 is displaced to the periphery of block 37 as shown, causing conduit 59 to be unobstructed by occluding element 49 and an intermediate port 46 to be aligned with conduit 59. Thus the compressed gas is able to flow via conduits 52, 53, 54 and 59 into the strap's internal cavity. When the cavity is sufficiently pressurized, e.g. to a pressure of 5 psi, the cavity pressure applies a force to spring actuated control valve 44 which is suitable to occlude conduit 52.

With respect to the embodiment of FIGS. 2 and 3, the actuator valve is able to be triggered when the strap free end 4 is sufficiently extended to cause strap adjustment chamber 6 of buckle frame 11 to be brought in abutting and force applying relation with the trigger protruding from front wall 2 of control device 5.

In another embodiment, a force is applied to the trigger by an initiating element of a strap restraining unit. The strap restraining unit, which is positioned forwardly from the control device, is configured to permit the strap free end to be speedily pulled without resistance until assuming a predetermined length which is sufficient to apply the hemorrhage suppressing force, whereupon a strap derived force causes displacement of the initiating element and the strap becomes restrained. The strap is subjected to a changing frictional force, such as a gradually increasing frictional force that ensures reliable and normally unreleasably locking capabilities. The strap restraining unit therefore facilitates one-handed deployment.

Figure 12:
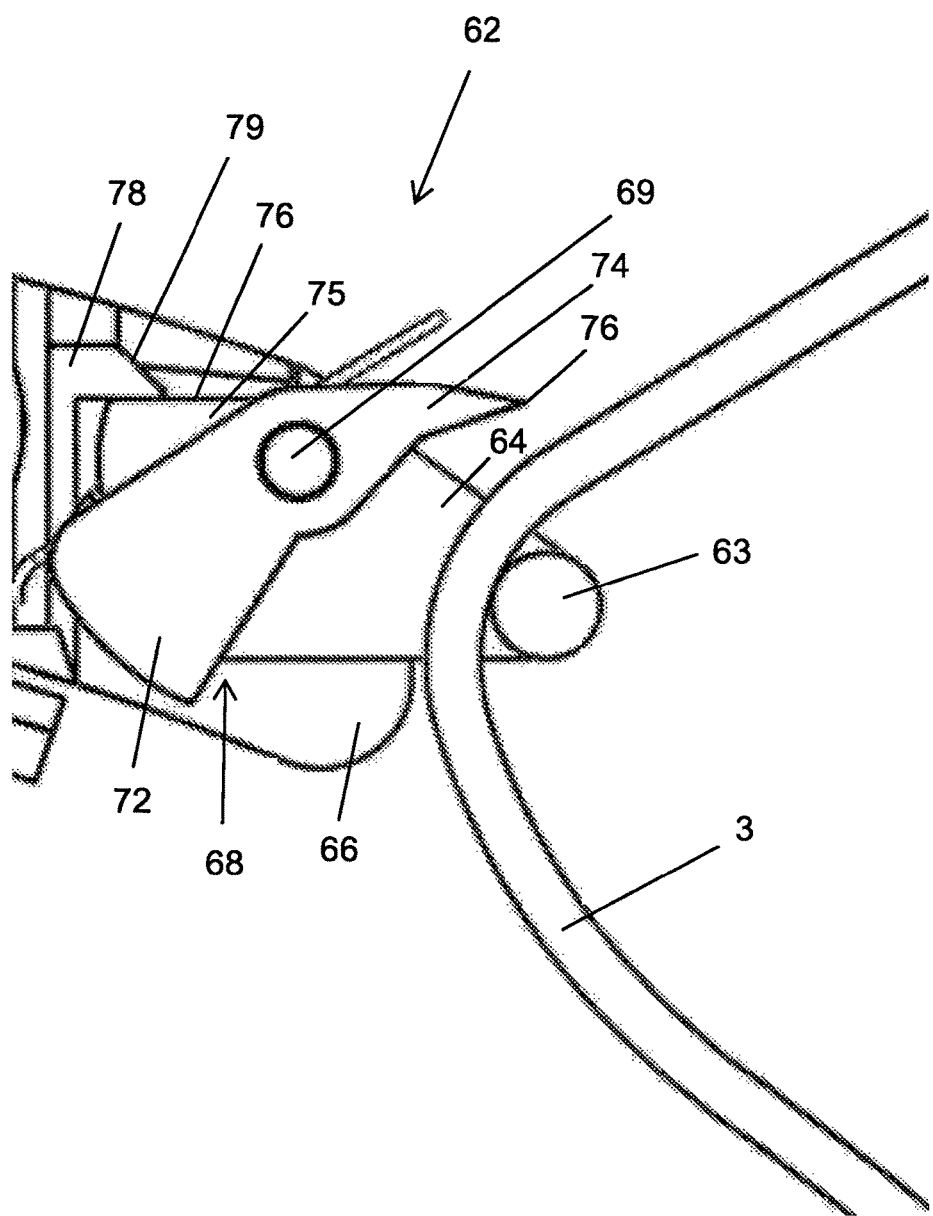
FIGS. 12-14 are three stages, respectively, of a strap restraining procedure according to one embodiment of the invention.
Figure 13:
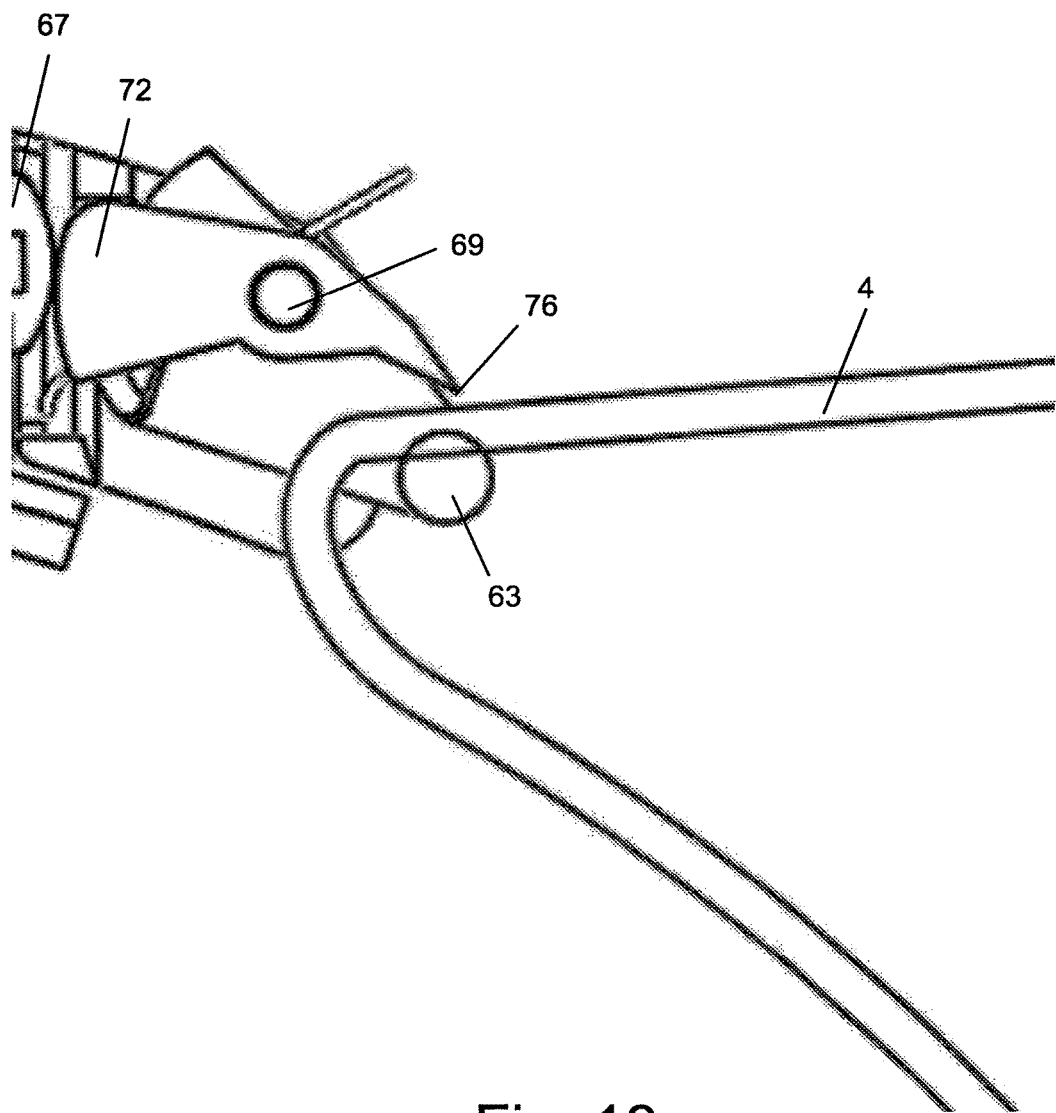
Figure 14:
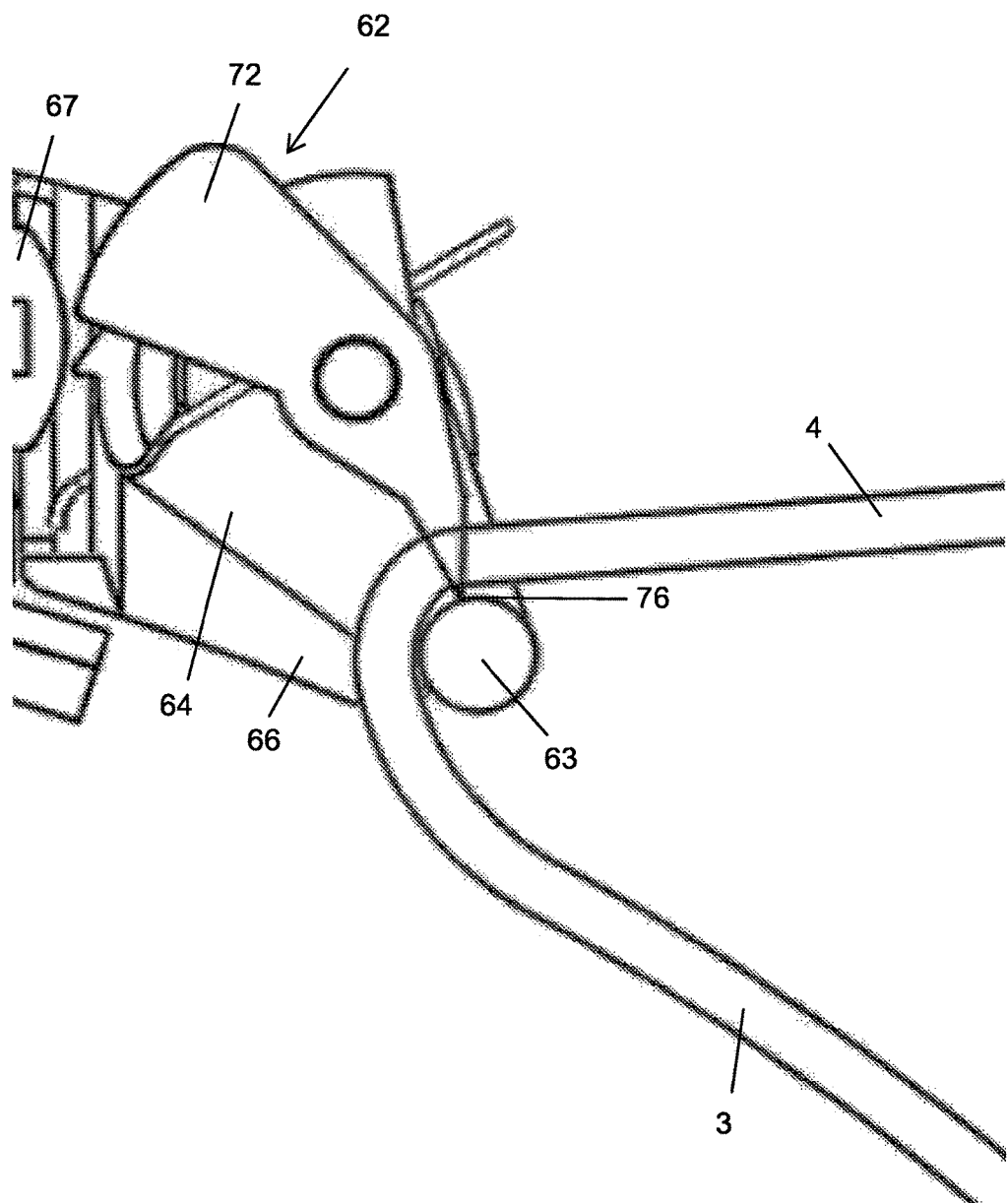

Strap restraining unit 62 illustrated in FIGS. 12-14 comprises a cylindrical arm member 63 that extends between two side elements 64, each of which is rotatably mounted by a corresponding swivel connection 69 to one of two laterally spaced and forwardly positioned appendages 66 of the buckle frame. A side element 64 is co-mounted with initiating-restraining member 68, which is also rotatable. Initiating-restraining member 68 has a relatively wide, rearwardly positioned initiating portion 72, which may be arcuate to subtend an angle of approximately 30 degrees, and a narrowing portion 74 positioned forwardly to swivel connection 69 to define serrated edge 76, which, when cooperating with arm member 63, serves to restrain the strap.

Initiating-restraining member 68 also has two laterally spaced shoulder elements 75. The upper planar edge 76 of a corresponding shoulder element 75 is releasably engageable from above with a thin cantilevered head element 78 having a forward angled edge 79 and which is laterally spaced from trigger 67.

In the initial stage of the strap restraining procedure shown in FIG. 12, strap 3 is positioned between serrated edge 76 and arm member 63, each shoulder element 75 is engaged by a corresponding head element 78 to prevent movement of initiating-restraining member 68 if arm member 63 is inadvertently contacted, and initiating portion 72 is forwardly spaced from trigger 67.

Upon extending free end strap portion 5, a force is applied onto arm member 63, as shown in FIG. 13, causing the latter to rotate about swivel connection 69 in a clockwise direction in accordance with the illustrated disposition such that the spacing between serrated edge 76 and arm member 63 is reduced. The applied force is sufficient to cause each shoulder element 75 to be disengaged from the corresponding head element 78 and to thereby permit rotation of initiating portion 72. The distance from the center of swivel connection 69 to the peripheral edge of initiating portion 72 is greater than the distance to the periphery of trigger 67 when the latter is in a normal rest position. Thus the rotation of initiating portion 72 in a clockwise direction will cause trigger 67 to be depressed and the predetermined dose of compressed gas to be discharged into the cavity of the strap 3.

In the final stage shown in FIG. 14, strap free end portion 4 is additionally extended causing initiating portion 72 to be separated from trigger 67, and serrated edge 76 bears on arm member 63 so as to restrain strap 3 positioned therebetween and to prevent additional movement of the latter.

Figure 15:
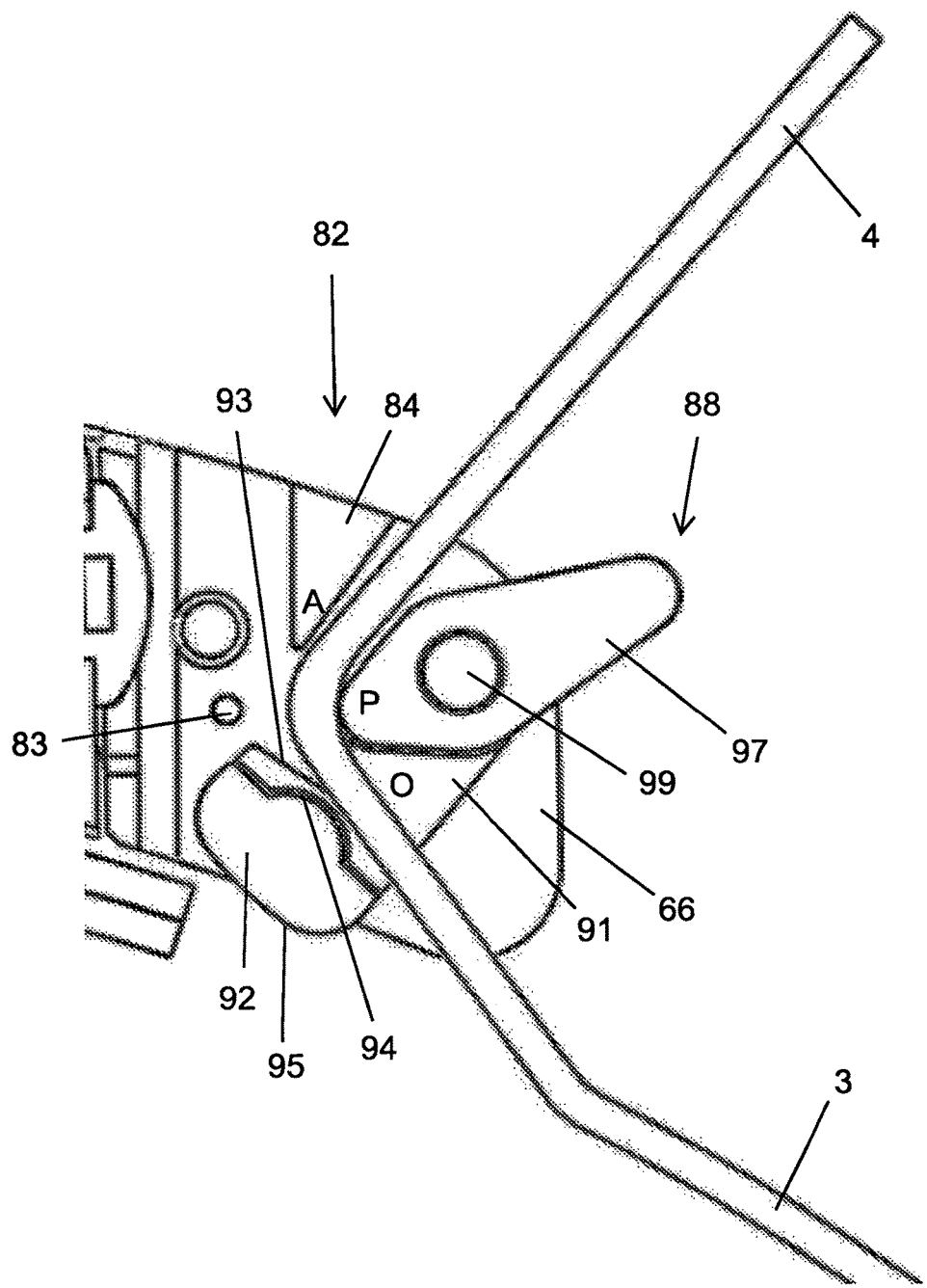
FIGS. 15-16 are two stages, respectively, of a strap restraining procedure according to another embodiment of the invention.
Figure 16:
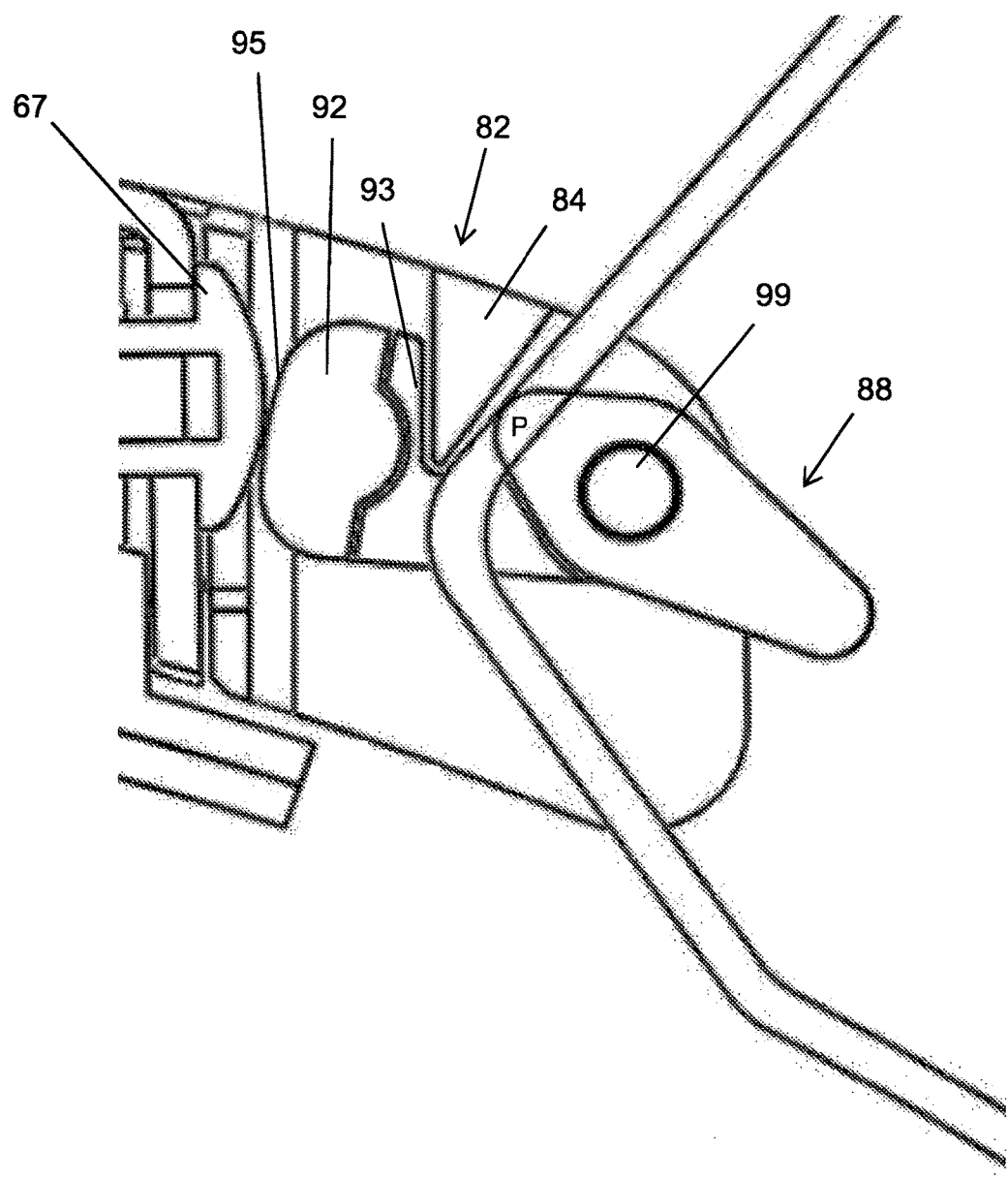

Strap restraining unit 82 illustrated in FIGS. 15 and 16 comprises a rotatable initiating-restraining member 88 that cooperates with a stationary triangular element 84. Triangular element 84, which laterally protrudes from the inner surface of laterally spaced and forwardly positioned appendages 66 of the buckle frame, has a downwardly pointing apex A and its upper surface may coincide with the upper edge of the appendages 66.

Unitary initiating-restraining member 88 has opposed side surfaces 91 that are adjacent to a corresponding appendage 66. An intermediate region of side surface 91 is formed with a V-shaped notch 93, for cooperation with the stationary triangular element 84. An elongated restraining portion 97, which may be elliptical, is positioned forwardly to notch 93. A pin holding section 92 is positioned rearwardly to notch 93. An opening O through which strap 3 is introducible is provided in the middle of member 88, below notch 93.

Restraining portion 97 has an intermediate tubular, laterally oriented cavity in which is fitted axle 99 rotatably mounted to the buckle frame appendages 66, to permit rotation of initiating-restraining member 88. Restraining portion 97 also has a rearwardly positioned strap abuttable protuberance P of a limited thickness, which may have a curved outer surface tangential to the adjoining edge of restraining portion 97 and laterally extends between the two side surfaces 91. The rearward rounded edge 95 of pin holding section 92 having a thickened, relatively large radius greater than that of restraining portion 97 and extending between the two side surfaces 91 constitutes the initiating portion.

In the initial stage of the strap restraining procedure shown in FIG. 15, initiating-restraining member 88 is obliquely disposed such that strap abuttable protuberance P points away from triangular element 84. As a result of this disposition, strap 3 is able to be fed through the interspace between triangular element 84 and strap abuttable protuberance P, and also between a guiding surface 94 of pin holding section 92, e.g. convex, and strap abuttable protuberance P, urging the strap to follow a curved path.

While the free end 4 of strap 3 is being pulled, a moment is applied to strap abuttable protuberance P as a result of the curved path of the strap and causes initiating-restraining member 88 to rotate about axle 99, in a clockwise direction according to the illustrated orientation, to achieve the orientation shown in FIG. 16 by which triangular element 84 is received within V-shaped notch 93 and strap abuttable protuberance P points towards triangular element 84. As a result of this disposition, the gap between triangular element 84 and strap abuttable protuberance P becomes reduced, and strap abuttable protuberance P is consequently caused to bear on strap 3 while pressing the latter onto the adjacent surface of triangular element 84. The combined pressing action and reduced gap causes strap 3 to be restrained, preventing a user to additionally displace the strap.

At this final stage, initiating portion 95 has been sufficiently rotated so as to cause trigger 67 to be depressed since the distance from the center of axle 99 to the edge of initiating portion 95 is greater than the distance to the periphery of trigger 67 when the latter is in a normal rest position.

As a further precaution to prevent reverse movement of strap 3, a spring mounted pin (not shown) may extend laterally outwardly from pin holding section 92 towards a corresponding appendage 66. After initiating-restraining member 88 has been sufficiently rotated, the pin is received in aperture 83 (FIG. 15) formed in appendage 66, causing initiating-restraining member 88 to be locked in position. A release element accessible from the outer surface of an appendage 66 may be actuated to cause the spring associated with the pin to become compressed and to thereby allow the pin to become disengaged from aperture 83.

FIGS. 20-25 illustrate another embodiment of a self-regulating flow control unit 144 wherein all of its components, with the exception of a spring, are made of inexpensive materials for reduced costs, such as polymeric materials.

Figure 20:
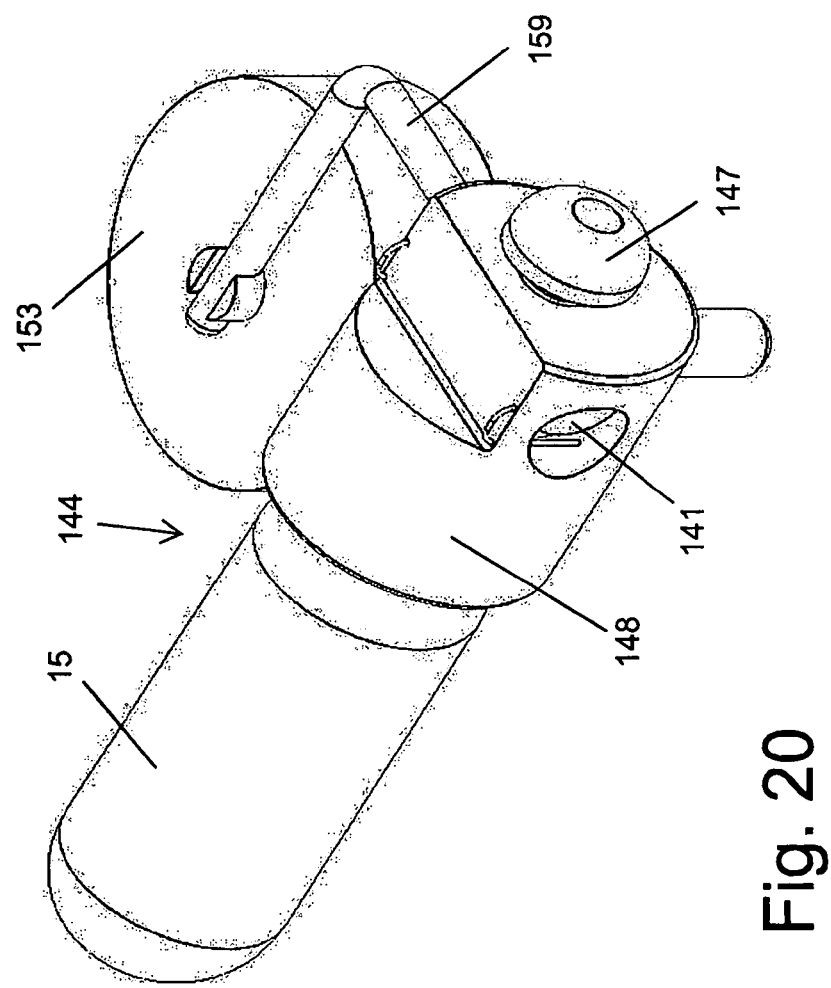
FIG. 20 is a perspective view of a flow control unit, according to another embodiment of the invention.

As shown in FIG. 20, flow control unit 144 comprises a rigid puncture pin carrier 148 which is displaceable with respect to compressed gas container 15, a piston assembly 153 for controlling the flow of the discharged compressed gas, and a pivotal valve member 159 driven by piston assembly 153 and having a closure element that is fitted in a bore 141 formed in carrier 148. Carrier 148, which has a cylindrical body although a portion of which may be removed for material savings, is displaceable in response to a force applied to trigger 147 protruding from, and engaged with, the body of carrier 148 by the initiating element of the strap restraining unit.

Figure 21:
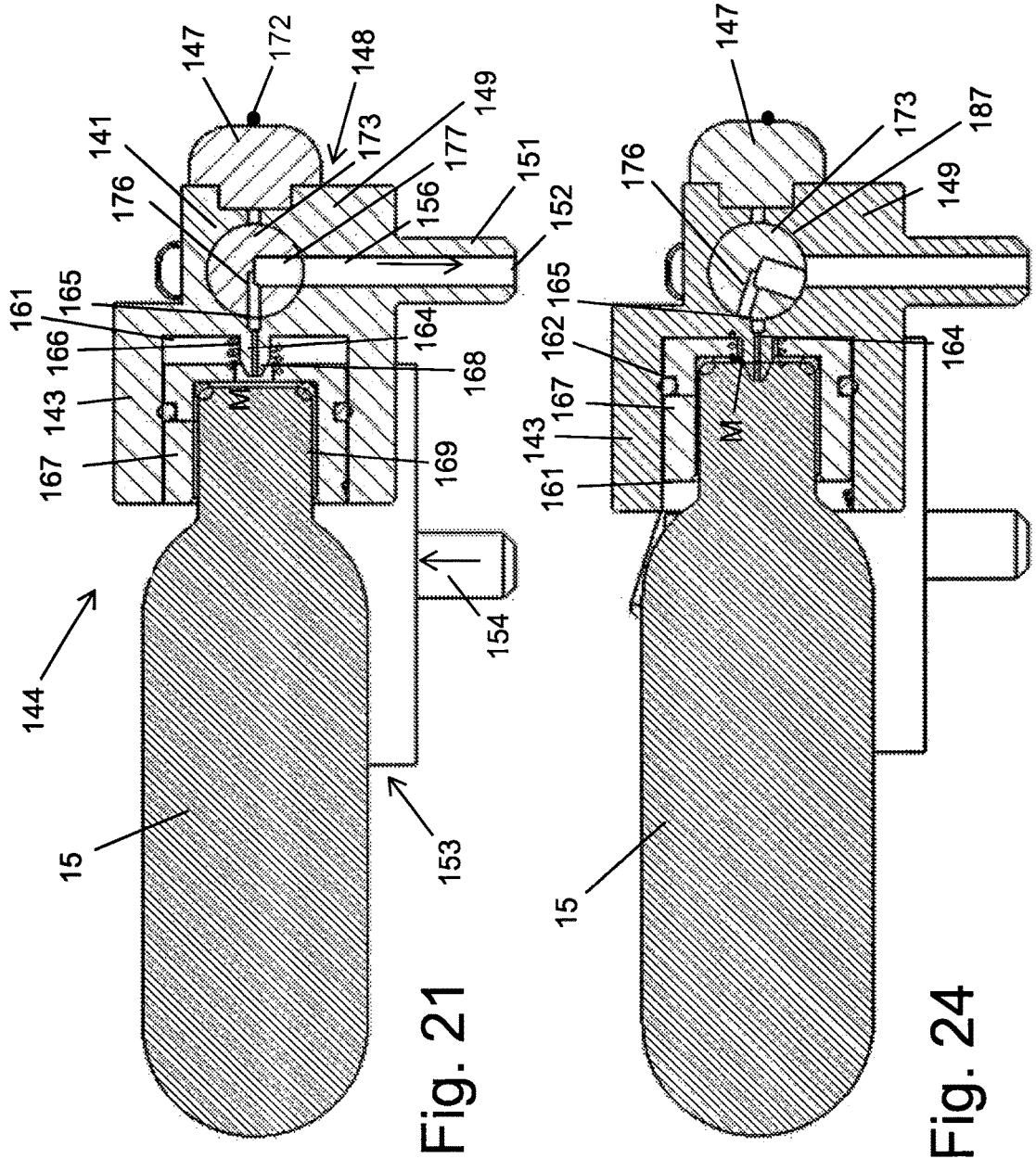
FIG. 21 is a vertical cross sectional view of the flow control unit of FIG. 20, cut along a plane coinciding with the longitudinal axis of a gas container, which is shown prior to being punctured.

A vertical cross section of flow control unit 144 is shown in FIG. 21. In order to control the pressure within the internal cavity of the strap, carrier 148 is configured with a connecting fitting 151 for insertion into the internal cavity of the strap in a pressure tight manner, to allow the discharged compressed gas to flow through inlet port 152 formed within fitting 151 to the internal cavity of the strap. Within connecting fitting 154 of piston assembly 153 for insertion into the internal cavity of the strap in a pressure tight manner is formed an outlet port, through which pressurized gas from the internal cavity of the strap is able to flow. The piston of assembly 153 causes the closure element to terminate the flow of compressed gas from container 15 when the pressure within the internal container rises above a predetermined level.

Carrier 148 is configured with a cylindrical container-facing body portion 143 and a truncated trigger-facing body portion 149 of a smaller height than portion 143.

A cylindrical cavity 161 is formed within, and coaxial with, the cylindrical container-facing body portion 143. Received in cavity 161 is annular stationary adaptor 167, with which gas container 15 is releasably engageable, e.g. threadedly engageable. Adaptor 167 may be stationary relative to carrier 148 by being connected to the housing of the control device. Alternatively, gas container 15 may be releasably secured to the control device housing, causing adaptor 167 to be stationary relative to carrier 148 when engaged with the gas container. Adaptor 167 is formed with a central aperture 168.

Hollow puncture pin 164 is fixed within protrusion 166 which protrudes from trigger-facing body portion 149 into cavity 161 and is aligned with central aperture 168 of adaptor 167 and with the longitudinal axis of threading 169, or any other annular engaging means adapted to be releasably engaged with gas container 15, and with the longitudinal axis of gas container 15 when engaged with the annular engaging means. A small bore 165 aligned with puncture pin 164 is formed within protrusion 166 and extends to the periphery of bore 141.

Cylindrical closure element 173 is in abutting relation with the outer wall of bore 141, and is formed with two angled bores 176 and 177, e.g. perpendicular to each other, which are in fluid communication with each other and extend to the outer wall of bore 141. In the illustrated disposition of closure element 173, bore 176 is aligned with bore 165, and bore 177 is aligned with channel 156 formed in trigger-facing body portion 149 and extending from inlet port 152 to the outer wall of bore 141, allowing the discharged pressurized gas to flow into the internal cavity of the strap when the membrane M of container 15 is punctured, shown in FIG. 24.

Figure 22:
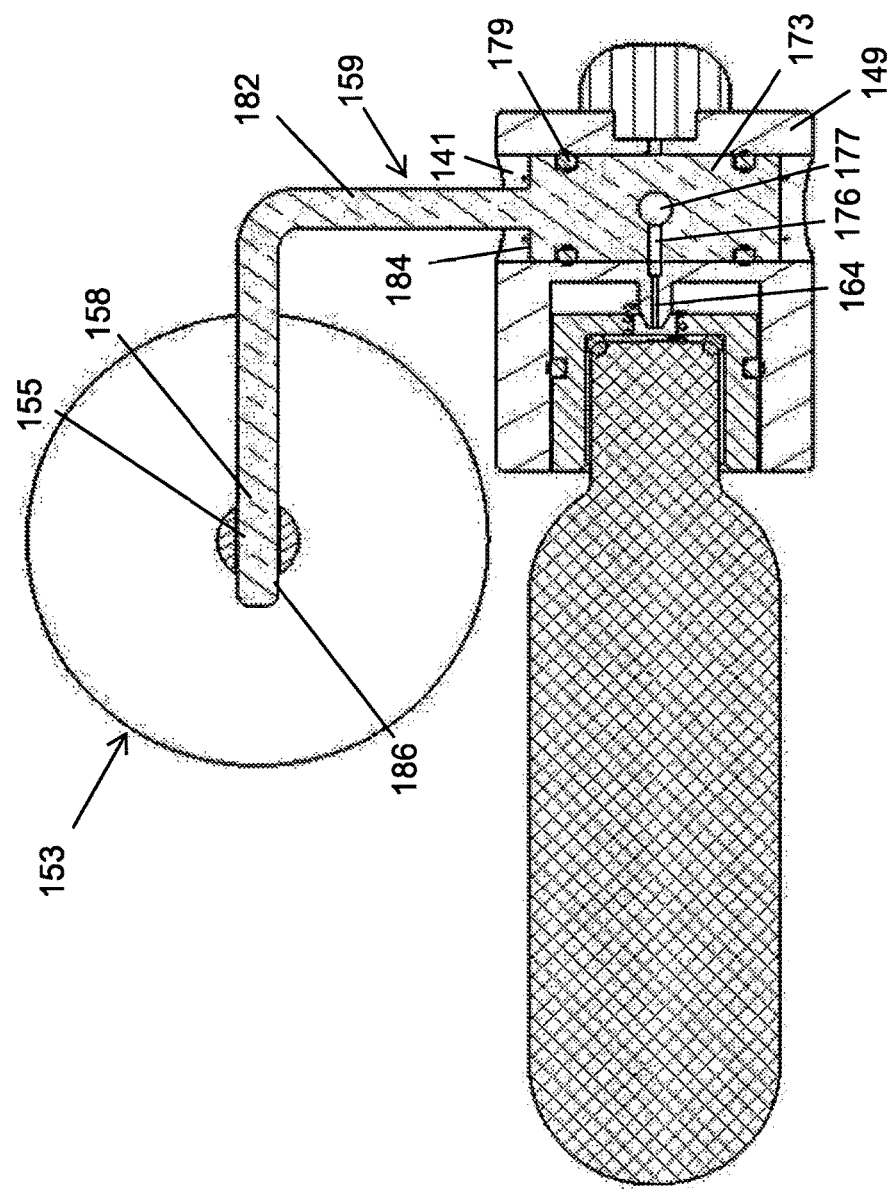
FIG. 22 is a horizontal cross sectional view of the flow control unit of FIG. 20, cut along a plane coinciding with the longitudinal axis of a gas container, which is shown prior to being punctured.

Valve member 159 functioning as a ball valve is shown in more detail in FIG. 22. Rotatable closure element 173 is slightly shorter than bore 141 formed in trigger-facing body portion 149. The diameter of closure element 173 is substantially equal to, and slightly smaller than, the diameter of bore 141. Closure element 173 is maintained in sealing engagement with the wall of bore 141 by spaced seal elements 179 that are received in corresponding circumferential seats. Bores 176 and 177 may be formed at the longitudinal centerline of closure element 173, in alignment with puncture pin 164.

An angled connecting arm 182, e.g. having two portions that are disposed at an angle of approximately 90 degrees from each other, extends from the end 184 of closure element 173 facing piston assembly 153. The free end 186 of connecting rod 182 is coupled to retainer element 155 protruding from the upper surface of the housing of piston assembly 153. Retainer element 155 is formed with an intermediate groove 158 within which angled arm 182 is movably received.

Referring now to FIG. 23, piston assembly 153 has an annular housing 157 that defines an internal cavity 171. The upper surface 178 of housing 157 is formed with an aperture 181 (FIG. 25) coincident with the retainer element groove and which is normally covered by the free end of angled arm 182. Outlet fitting 154 extends downwardly from a central portion of fitting holder 163, which is secured to the bottom end of housing 157. A channel 175 aligned with aperture 181 is formed in outlet fitting 154, and extends from outlet port 174 to the upper surface of fitting holder 163.

Piston 188, which is sealingly engaged with the inner surface of housing 157, has a central head portion 189 that is aligned with, and has smaller dimensions than, aperture 181 formed in upper surface 178 of housing 157. Spring 192 surrounding head portion 189 is connecting to the adjacent portion of housing 157, and is biased such that piston 188 is normally in abutting relation with fitting holder 163, as illustrated. Compressed gas flowing through channel 175 is able to act on piston 188.

Referring now to FIG. 24, carrier 148 is caused to be displaced with respect to adaptor 167 within cavity 161 after a force is applied to trigger 147 by the initiating element of the strap restraining unit. Seal element 162 positioned between container-facing body portion 143 and adaptor 167 urges carrier 148 in a linear displacement. As a result of the linear displacement, which is limited by contact between trigger-facing body portion 149 and adaptor 167, puncture pin 164 punctures membrane M. Compressed gas is consequently discharged from container 15 to the internal cavity of the strap via puncture pin 164 and channel 156, as indicated by the downwardly extending arrow in FIG. 21, and also flows through outlet fitting 154, as indicated by the upwardly extending arrow in FIG. 21.

The pressure within the internal cavity is gradually and continuously increased while the compressed gas is being discharged. At the same time, piston 188 is caused to be upwardly displaced gradually within cavity 171 by the compressed gas flowing through channel 175, as illustrated in FIG. 25.

When piston 188 is upwardly displaced, spring 192 is compressed and head portion 189 protrudes through aperture 181. The upwardly displaced head portion 189 consequently contacts the free end of arm 182 and causes the latter to be pivoted about retainer element 155 (FIG. 22), generating a moment which causes closure element 173 to slightly rotate about the longitudinal axis of bore 141 in a clockwise direction according to the illustrated orientation, e.g. a rotation of up to 20 degrees. The free end of arm 182 functions as a lever, by which the required force applied by piston 188 that is needed to counteract the high pressure of gas discharged from the gas container is able to be reduced. As a result of this rotation, bore 176 is no longer aligned with puncture pin 164 and the periphery 187 of closure element 173 occludes bore 165, preventing additional discharge of compressed gas. By virtue of this arrangement, a predetermined pressure, e.g. 5 psi, which is generally a function of the resistance of spring 192 may be speedily achieved within the internal cavity of the strap, but not surpassed, and likewise a corresponding substantially constant hemorrhage suppressing force will be applied onto the limb with which the strap is engaged. Also, the remaining compressed gas may be used for an additional hemorrhage suppression operation since the gas container becomes isolated from the internal strap cavity to prevent additional discharge of the compressed gas.

If the internal pressure within the strap cavity drops, for example due to leakage, piston 188 will be downwardly displaced and the free end of arm 182 returns to its original position shown in FIG. 23. Closure element 173 is therefore caused to rotate in a counterclockwise direction to achieve alignment of the bores shown in FIGS. 21 and 22, resulting in an additional dose of compressed gas to be discharged to the internal cavity of the strap, until the predetermined pressure is once again achieved.

A button 172, or any other switching device, may be connected to circuitry for activating the digital timer. Accordingly, the force applied to trigger 147 by the initiating element of the strap restraining unit will not only result in tensioning of the strap, puncturing of the gas container membrane, and regulating the pressure within the internal cavity in response to the discharge of pressurized gas, but will also set the starting time of a hemorrhage suppressing operation. A medic treating a subject will be able to view on the timer the elapsed time after the hemorrhage suppressing force was initiated in order to avoid irreversible muscle damage resulting from prolonged ischemia.

It will be appreciated that other configurations of a flow control unit housed within the control device are also within the scope of the invention. The target controlled pressure may be adjusted, such as by manually or electrically applying a force onto the spring in order to change the spring resistance, so that the applied hemorrhage suppressing force will be suitable for different sized subjects, such as an infant or an obese person.

Figure 17:
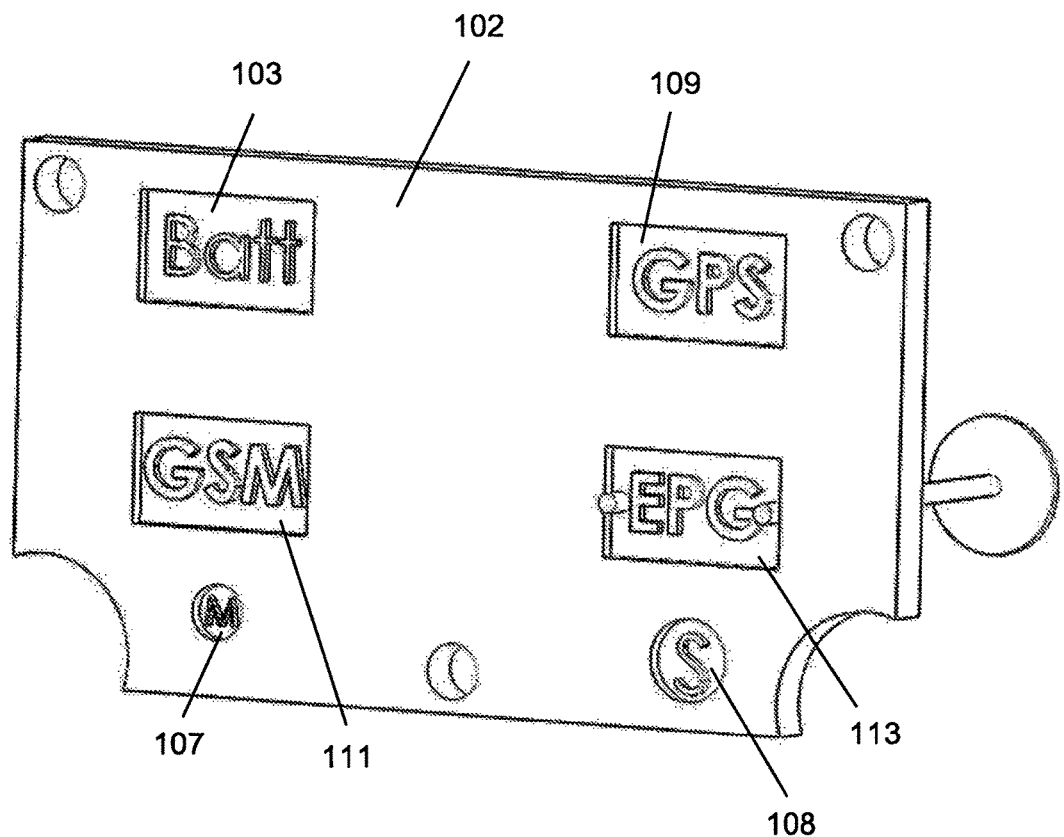
FIG. 17 is a schematic illustration of a circuit board for supporting the functionality of various electronic devices that are intended to assist a wounded victim.

In another embodiment of the invention, the control device comprises a microprocessor provided in the schematically illustrated circuit board 102 shown in FIG. 17, for supporting the functionality of various electronic devices that are able to assist a wounded victim.

The following are some of the components and modules that are able to be provided in circuit board 102: (1) battery 103 or any other power source for energizing the various components and modules, (2) microphone 107 for recording messages or for communicating with others, for example to request assistance, (3) speaker 108 for listening to messages or instructions recorded by microphone 107 or imported from a database, or for communicating with others, (4) a Global Positioning System (GPS) 109 for locating the wounded person, (5) a Global System for Mobiles (GSM)

111 for transmitting the GPS data or communicating with a hospital, such as by voice based communication channels, textual messages, or emergency signals, and (6) an Electronic Pulse Generator (EPG) 113 for supplying constantly generated pulses to the wounded person, for example by means of a patch attached to the skin, to prevent him or her from fainting or becoming subconscious.

Figure 18:
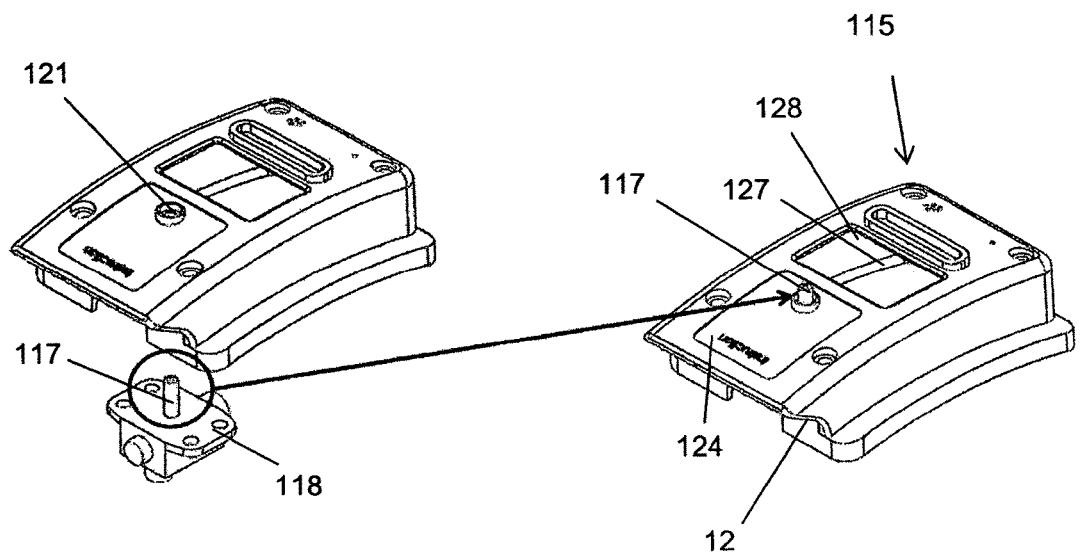
FIG. 18 is a perspective view of a tourniquet based control device, according to another embodiment of the invention.

In the embodiment of FIG. 18, control device 115 comprises further means for assisting the wounded person. For example, an illumination device 127 functioning as an in-field detection light for easily locating the wounded person, which may be activated by electrical or chemical means, is mounted in an aperture 128 centrally located in the upper surface of control device 115, and may be positioned underneath the digital timer.

A tubular connection 117 of a Luer lock 118 is insertable through a port 121 located in the vicinity of rear wall 12, to enable rapid connection to hospital devices and instruments so as to reduce risks of hemorrhaging and ischemia.

Surrounding tubular connection 117 is a printable surface 124, e.g. a card or sticker, on which are written instructions for treating wounded victims in general, or the given wounded person specifically. Emergency phone numbers may also be printed on printable surface 124. A medic may also receive such instructions by playing back a recorded message and hearing the message over the speaker.

Figure 19:
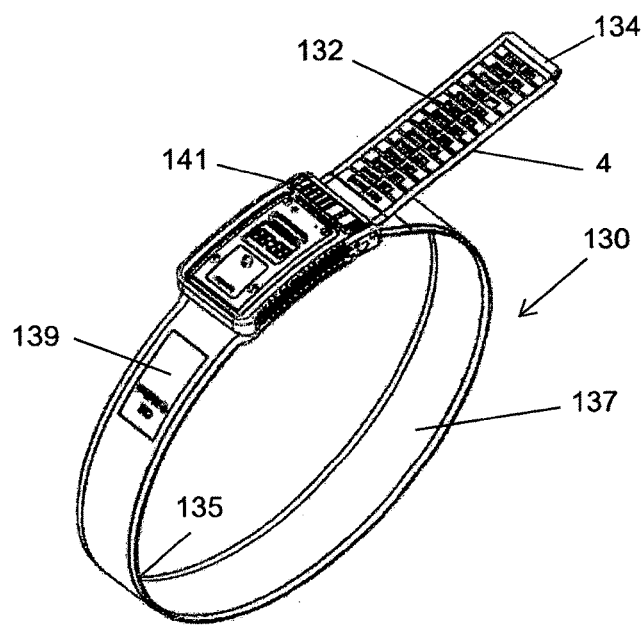
FIG. 19 is a perspective view of a tourniquet according to another embodiment of the invention.

Tourniquet 130 shown in FIG. 19 is provided with one or more of the following additional features for assisting a wounded victim: (1) a limb diameter scale 132 printed on the free end 4 of the strap, for indicating the diameter of the limb to which a hemorrhage suppressing force is desired to be applied, (2) a wrapped morphine capsule, or a capsule of any other powerful pain relief drug, inserted in a dedicated cavity 134 formed in the forward end of the strap, (3) a drug transfer patch 135 applied to the inner face of the strap, (4) a hydrophobic coating 137 applied to the strap, to prevent excreted liquids such as blood to adhere to the strap and then to the skin, a feature of particular benefit to burn victims, (5) a cardiopulmonary resuscitation (CPR) assistance card 139 applied to the outer face of the strap, for example in the form of a sticker on which is imprinted CPR guidelines or in the form of a media card in which voice information related to the CPR guidelines is recorded and then is able to be played back over the speaker, and (6) an identification region, for example in the form of a barcode, for identifying the wounded person, detailing wound details or operations carried out by the medic, or purchasing the tourniquet at a store.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

What is claimed is:

1. An intelligent pneumatic tourniquet, comprising:
a) a control device which is locally attached to an inflatable strap having an internal cavity, for achieving a predetermined pressure within said cavity and for thereby applying a required hemorrhage suppressing force onto a limb with which said strap is engaged, wherein said control device comprises a compressed gas container, a flow control unit that is in fluid communication with said container and with said internal cavity, and a rigid housing within which said compressed gas container and said flow control unit are retained; and
b) a strap restraining unit for triggering said flow control unit by an initiating force applied thereby, wherein said flow control unit, when triggered, is configured to selectively supply a dose of pressurized gas discharged from said gas container to said internal cavity,
wherein said flow control unit comprises a slidable puncture pin carrier and an abutment protruding from said carrier, a triggering force being transmitted from said abutment to said carrier to initiate puncturing of a membrane of said compressed gas container and resulting discharge of said compressed gas into said internal cavity of said strap.

2. The tourniquet according to claim 1, wherein the flow control unit comprises a slidable actuator valve which, when triggered, causes a conduit to be unobstructed and to thereby allow the discharged compressed gas to flow therethrough into the internal cavity of the strap.

3. The tourniquet according to claim 1, wherein the flow control unit further comprises a valve having a closure element in fluid communication with the puncture pin, said closure element operable to occlude a fluid passageway extending from the puncture pin when the pressure within the internal cavity of the strap exceeds a predetermined level.

4. The tourniquet according to claim 3, wherein the flow control unit further comprises a piston assembly on which the discharged compressed gas acts and which is operable to drive the valve member.

5. The tourniquet according to claim 4, wherein the closure element is cylindrical and rotatable, and is in sealing engagement with a wall of a bore formed in the puncture pin carrier, and wherein an angled connecting arm with a free end extends from an end of the closure element and is movably received within an intermediate groove of a retainer element protruding from an upper surface of a housing of the piston assembly, said free end being contacted by a head portion of a piston of the piston assembly during upward displacement thereof and compression of a spring surrounding said head portion caused by the discharged compressed gas and generating a moment to cause rotation of the closure element about a longitudinal axis of the bore and occlusion of the fluid passageway.

6. The tourniquet according to claim 1, wherein the strap restraining unit is configured to permit displacement of a free end of the strap without resistance until said free end assumes a predetermined length which is sufficient to apply the hemorrhage suppressing force and to cause the strap to become restrained by a strap derived force.

7. The tourniquet according to claim 6, wherein the strap restraining unit is configured to cooperate with the flow control unit so as to facilitate maximum tensioning of the strap, puncturing of the gas container membrane and regulating the pressure within the internal cavity to maintain the predetermined pressure in response to a single user motion.

8. The tourniquet according to claim 6, further comprising a digital timer, circuitry for activating said digital timer and a trigger-mounted button connected to said circuitry for sensing the initiating force applied by the strap restraining unit, said timer, button and circuitry being mounted in the housing of the control device on which is displayable elapsed time of the hemorrhage suppressing operation.

9. The tourniquet according to claim 1, wherein the control device comprises a microprocessor-based circuit board for supporting the functionality of one or more electronic devices that are intended to assist a wounded victim.

10. The tourniquet according to claim 1, further comprising a trigger protruding from a body of said flow control unit, wherein the strap restraining unit comprises:
   i. a guide element, for urging the strap, when introduced through an interspace of the strap restraining unit, to follow a curved path; and
   ii. a rotatable initiating-restraining member mounted by a swivel connection to a frame element, said initiating-restraining member comprising a restraining element and an initiating element and adapted to rotate about said swivel connection in response to a strap derived force resulting from displacement of a free end portion of the strap through the strap restraining unit and along said curved path,
   wherein the strap is positioned between said restraining element and said guide element at an initial stage of a strap restraining procedure, a distance from a center of said swivel connection to a peripheral edge of said initiating element is greater than a distance from the center of said swivel connection to a periphery of said trigger, and said initiating element is positioned forwardly spaced from said trigger,
   wherein said initiating-restraining member is rotated about said swivel connection following extension of said free end strap portion without resistance along said curved path in a stage subsequent to said initial stage in response to said strap derived force, causing a spacing between said restraining element and said guide element to be reduced, said initiating element to depress said trigger by an initiating force due to the greater distance of the initiating element peripheral edge from the center of said swivel connection than the distance from the trigger periphery to the center of said swivel connection, and by an initiating force applied thereby,
   wherein said puncture pin carrier, after being triggered, is configured to be displaced to initiate puncturing of a membrane of the compressed gas container, so that the flow control unit will selectively supply a dose of the pressurized gas discharged from the gas container to the internal cavity at the predetermined level, to apply the required hemorrhage suppressing force,
   wherein said initiating-restraining member is additionally rotated about said swivel connection following additional extension of said free end strap portion along said curved path in a final stage of the strap restraining procedure, causing said initiating element to be separated from said trigger and said restraining element to be in sufficiently close pressing relation with said guide element so as to prevent additional movement of the strap which is positioned therebetween.

11. The tourniquet according to claim 10, wherein the guide element is a cylindrical arm member that extends between two side elements which are co-mounted with the initiating-restraining member.

12. The tourniquet according to claim 11, wherein the initiating-restraining member also comprises two shoulder elements each of which is releasably engageable by a corresponding head element during the initial stage of the strap restraining procedure to prevent movement of the initiating-restraining member if the arm member is inadvertently contacted, application of the strap derived force being sufficient to cause each of said shoulder elements to become disengaged from said corresponding head element and to permit rotation of the initiating element.

13. The tourniquet according to claim 10, wherein the guide element is a stationary triangular element and the initiating-restraining member is configured with a notch for cooperating with said triangular element.

14. The tourniquet according to claim 13, wherein the initiating-restraining member is further configured with a pin holding section from which laterally extends a spring-mounted pin for locking the initiating-restraining member in position after having been rotated in the stage subsequent to the initial stage.

15. A tourniquet equipped strap restraining unit, comprising:
   a) a guide element for introduction therethrough of a pneumatically inflatable strap adapted to apply a hemorrhage suppressing force onto a limb of a wounded subject;
   b) a restraining element which is movable in response to a strap derived force resulting from displacement of said strap through said strap restraining unit; and
   c) an initiating element that is also movable in response to the strap derived force so as to be displaceable to a position at which it is capable of applying a force to a trigger for actuating inflation of said strap, wherein said strap restraining unit is configured to permit displacement of a free end of said strap without resistance until said free end assumes a predetermined length which is sufficient to apply the hemorrhage suppressing force and which corresponds to a disposition of said restraining element at which it is in sufficiently close pressing relation with said strap to cause said strap to become restrained.

16. A tourniquet, comprising:
   a) a flexible strap;
   b) a large-area part locally attached to, and protruding outwardly from, a first longitudinal end of said strap, wherein said protruding part has a base configured to be placed in abutting relation with a wounded limb to which a hemorrhage suppressing force is desired to be applied as well as an outer surface, each region of said outer surface being spaced by a substantially uniform distance from a corresponding region of said base; and
   c) a buckle frame which is engageable with said protruding part, said buckle frame being attached to a second longitudinal end of said strap such that a strap free end portion extends from, and is movably engageable with, said buckle frame,
   wherein, when said protruding part is placed in abutting relation with the wounded limb and said strap is wrapped about the limb to cause said buckle frame to be adjacent said protruding part, an unattached end of said buckle frame is engageable with a portion of said protruding part which is proximate to said first end of said strap and a strap-connected end of the buckle frame is engageable with an unattached end of said protruding part which is distant to said first end,
   wherein, when said buckle frame is engaged with said protruding part, extension of said strap free end portion causes said strap to become sufficiently tensioned so as to apply circumferential pressure onto the limb and to induce hemorrhage suppression.

17. The tourniquet according to claim 16, wherein the buckle frame surrounds, and is of a same shape as, the protruding part.

18. The tourniquet according to claim 16, wherein the strap is an inflatable strap having an internal cavity and the protruding part comprises a compressed gas container and a flow control unit that is in fluid communication with said container and with said internal cavity in order to achieve a predetermined pressure within said cavity.

19. The tourniquet according to claim 16, which is provided with one or more of the following features for assisting a wounded victim:
  i. a limb diameter scale printed on a free end portion of the strap, for indicating the diameter of the limb to which the hemorrhage suppressing force is desired to be applied;
  ii. a capsule of a pain relief drug inserted in a dedicated cavity formed in an end of the free end portion of the strap;
  iii. a drug transfer patch applied to an inner face of the strap;
  iv. a hydrophobic coating applied to the strap, to prevent excreted liquids to adhere to the strap and then to the skin;
  v. a cardiopulmonary resuscitation (CPR) assistance imprinted or media card applied to an outer face of the strap to provide CPR guidelines; and
  vi. an identification region, for identifying the wounded victim, detailing wound details or operations carried out by a medic, or purchasing the tourniquet.

20. A method for deploying a tourniquet, comprising the steps of:
  a) providing a tourniquet with a strap, a large-area part locally attached to, and protruding outwardly from, a first longitudinal end of said strap, and a buckle frame of a same shape as, and engageable with, a periphery of said protruding part, said buckle frame being attached to a second longitudinal end of said strap such that a strap free end portion extends from, and is movably engageable with, said buckle frame;
  b) placing said protruding part in abutting relation with a wounded limb to which a hemorrhage suppressing force is desired to be applied;
  c) positioning said strap about said limb until said buckle frame is adjacent to said protruding part;
  d) engaging an unattached end of said buckle frame with a portion of said protruding part which is proximate to said first end;
  e) after said unattached end of said buckle frame is engaged with said portion of said protruding part which is proximate to said first end, engaging a strap-connected end of said buckle frame with a portion of said protruding part which is distant to said first end; and
  f) extending said strap free end portion until said strap becomes sufficiently tensioned so as to apply circumferential pressure onto said limb and to induce hemorrhage suppression.

21. The method according to claim 20, wherein the strap is an inflatable strap having an internal cavity and the protruding part comprises a compressed gas container and a flow control unit that is in fluid communication with said container and with said internal cavity in order to achieve a predetermined pressure within said cavity, the method further comprising the step of maximum tensioning of the strap, puncturing of a membrane of said gas container and regulating the pressure within said internal cavity to maintain the predetermined pressure in response to a single user motion.

22. The method according to claim 21, wherein the single user motion is associated with one handed motion.

* * * * *